United States Patent
Menke et al.

[11] Patent Number: 5,872,328
[45] Date of Patent: Feb. 16, 1999

[54] FERROCENE DERIVATIVES

[75] Inventors: Klaus Menke, Bruchsal; Jutta Böhnlein-Mauss, Speyer; Klaus-Peter Brehler, Ulm; Jubert Jungbluth, Kaarst; Horst Neitsch, Gelsenkirchen, all of Germany

[73] Assignees: Chemische Betriebe Pluto GmbH, Herne; Fraunhofer Gesellschaft zur Forderung der angewandte Forschung e.v., Munich, both of Germany

[21] Appl. No.: 810,469

[22] Filed: Mar. 4, 1997

[30] Foreign Application Priority Data

Mar. 6, 1996 [DE] Germany ............ 196 08 627.2

[51] Int. Cl.$^6$ ................ C06B 45/10; C07F 17/02
[52] U.S. Cl. ................ 149/19.2; 149/19.4; 149/19.5; 149/19.9; 556/143
[58] Field of Search ............ 556/143; 149/19.2, 149/19.4, 19.5, 19.9

[56] References Cited

U.S. PATENT DOCUMENTS

| | | | |
|---|---|---|---|
| H717 | 12/1989 | Stephens et al. | 149/19.2 |
| 3,874,957 | 4/1975 | Corley et al. | 149/5 |
| 3,878,233 | 4/1975 | Nielsen | 260/439 CY |
| 3,968,126 | 7/1976 | Norris | 260/346.1 M |
| 4,023,994 | 5/1977 | Arendale | 149/19.2 |
| 4,318,760 | 3/1982 | Stephens et al. | 149/19.2 |
| 5,281,286 | 1/1994 | Sayles | 149/3 |

*Primary Examiner*—Porfirio Nazario-Gonzalez
*Attorney, Agent, or Firm*—Antonelli, Terry, Stout & Kraus, LLP

[57] ABSTRACT

New ferrocene derivatives with the general formula:

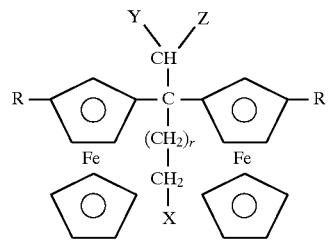

are described with

X=H or OH
Y=H or $CH_2OH$
Z=$(CH_2)_s$—$CH_2OH$
R=straight-chain or branched alkyl residue with 2 to 6 C atoms
r=0 to 8, preferably 0 to 2
s=0 to 8, preferably 1 and 2

These ferrocene derivatives are best suited as burning rate modifiers in composite solid propellants for rocket engines and gas generators.

25 Claims, 1 Drawing Sheet

FERROCENE DERIVATIVES

The invention relates to ferrocene derivatives with the general formula

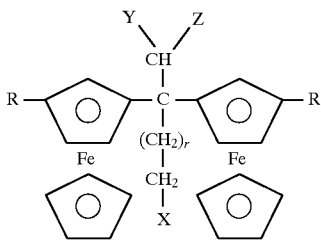

with
X=H or OH
Z=(CH2)$_s$—CH$_2$OH
R=straight-chain or branched alkyl residue with 2 to 6 C atoms
r=0 to 8, preferably 0 to 2
s=0 to 8, preferably 1 and 2
as well as their use.

Ferrocene derivatives are used as burning rate modifiers for solid rocket propellants. In this application they are used preferably in composite propellants containing ammonium perchlorate. When added in small quantities they significantly increase burning rates at low pressure and simultaneously lower the pressure exponent that describes the exponential rise in burning rate with increasing pressure according to Vieille's law.

The formula is:

$$r = A \cdot p^n$$

where r=burning rate
a=constant
p=pressure
n=pressure exponent

Pressure exponent n, which is frequently n=0.5 to 0.6 for fast-burning composite propellants, is reduced to a value of n=0.4 to 0.4 by adding a ferrocene derivative to the propellant.

Substituted ferrocene derivatives have proven effective for composite propellants with hydroxy terminated polybutadienes as binders, said derivatives being liquid, of low viscosity, completely miscible with the binder, and readily workable into the propellant. Frequently n-butylferrocene or 2, 2-(bisethylferrocenyl)propane, also identified by old brand names such as Catocen®, are used. However, they exhibit the undesired property of migration, in other words they migrate out of the rubber-elastic binder matrix of the propellant into the surrounding insulation. This results in irregular combustion, deterioration of resistance to aging, and possibly the formation of highly sensitive boundary layers.

To solve this problem, relatively complex ferrocene derivatives have been developed that exhibit significantly reduced or even absent migration behavior. One polymer bonded derivative that meets these requirements is Butacen® (see EP 169 130 and EP 171 307). Butacen® contains a ferrocene complex bonded to a polybutadiene prepolymer by a hydrocarbon spacer and a silane coupling reagent. It can be worked readily into a composite propellant that contains ammonium perchlorate, aluminum, and hydroxy terminated polybutadiene as binders. Due to the low content of active iron complex, however, a very much larger amount must be added in order to achieve the same effect of increasing the burning rate as a migrating ferrocene derivative. In addition, Butacen® is only obtainable by a costly and complex manufacturing process. The larger amount to be added and its costly manufacture mean that it costs much more to use than Catocen® or n-butylferrocene.

There are also developments (for example U.S. Pat. No. 3,932,240) in which ferrocene derivatives with hydroxyl or isocyanate end groups are bonded by a reaction in the plastic matrix of the solid propellant. These ferrocene derivatives are frequently not miscible with the reactive binder systems of conventional rocket propellants or adversely affect the pourability and processability of the propellant slurry to a significant degree as well as the mechanical properties of the finished propellant.

Methods are known from U.S. Pat. No. 3,878,233 and U.S. Pat. No. 3,957,840 for making diferrocenylpentanolene, especially 4,4'-diferrocenylpentanol-1. The suitability of the latter substance as a burning modifier is described in U.S. Pat. No. 3,932,240. This substance however is solid in the basic state and cannot be worked into the propellant at a high concentration. It therefore does not meet an important condition for propellant manufacture, namely being capable of being easily incorporated.

The goal of the present invention is to provide novel ferrocene compounds. They are intended to be especially suited as burning rate modifiers for solid propellants. For this application they should have a good burning behavior, not migrate, and be easier to synthesize than known, non-migrating burning rate modifiers. In addition they should have a high iron content relative to the molecular weight, a low viscosity, and a low vapor pressure.

This goal is achieved according to the invention by ferrocene compounds according to Claim 1.

The ferrocene compounds according to the invention can be used both as individual compounds and as mixtures in solid propellants. Preferably they are contained in solid propellants in amounts from 0.1 to 6.0 wt. % based on the total amount of solid propellant.

The compounds according to the invention have a liquid consistency with a viscosity that is not too high, as well as good miscibility with the binder polymers and, because of their OH groups, they have a clear, reproducible bonding function with constant equivalence values or OH numbers. They guarantee a constant pouring viscosity of finished mixed propellant slurries without negatively affecting the curing reaction or potting time. They also do not show any significant adverse effects on the rubber-elastic properties of the binder polymers. They are oxidation-stable in the solid propellant matrix so that the stability of the propellant is not adversely affected. The properties of the propellant from the safety standpoint are not negatively affected by incorporating the substances according to the invention. Migration is practically completely suppressed by directly incorporating these ferrocene compounds into the polymer structure of the propellant matrix.

The ferrocene derivatives according to the invention can theoretically be produced in the same manner as the substances described in U.S. Pat. No. 3,878,233. Suitable starting materials include for example ketomonocarboxylic acids such as acetocetic acid, 3-acetylpropionic acid, or 4-acetylbutyric acid. Ferrocene derivatives according to the invention with two functional OH groups can be obtained by using ketodicarboxylic acids such as 3-oxoglutaric acid or 4-oxopimelic acid or acetylated dicarboxilic acid such as 2-acetylsuccinic acid or 2-acetylglutaric acid as the starting material. Preferably the esters of the above acids, especially esters from reactions with low-molecular-weight alcohols, particularly methanol, can be used as starting materials.

Reaction of these substances with alkyl ferrocene to form the derivatives according to the invention preferably proceeds with an acid catalyst. Then the carboxyl and ester groups are reduced to $CH_2OH$ groups. Preferably this is performed by catalytically activated hydrogen (for example zinc in glacial acetic acid) or lithium aluminum hydride).

The invention also applies to the use of the ferrocene derivatives according to the invention as burning rate modifiers in solid propellants for rocket engines and for gas generators.

Preferably a solid propellant of this kind, also called a composite solid propellant, contains a crystalline inorganic oxidant, a binder with a liquid multiply-OH-substituted prepolymer, at least one linking reagent, and additional conventional additives such as polymer-specific plasticizers, antioxidants, and adhesion promoters. The containing ferrocene derivative according to the invention is coupled directly to the binder by the linking reagent.

The ferrocene derivatives proposed according to the invention can be incorporated especially advantageously in polyurethane binders whose prepolymer is a hydroxy terminated polybutadiene (HTPB), polyesterpolyol, or polyetherpolyol. The hydroxy terminated polyurethane prepolymers preferably have an OH functionality of 2 to 3 and a specific average molecular weight. In the case of HTPB this value is 400 to 4000, preferably 1000 to 3000. On the other hand, the hydroxy terminated polyester and polyether prepolymers have a preferred average molecular weight of 300 to 3000, preferably 800 to 2000.

Di- and/or trifunctional isocyanates are used as the linking reagents, preferably isophorondiisocyanate (IPDI), hexamethylenediisocyanate (HDI), dimeryldiisocyanate (DDI), toluene diisocyanate (TDI), or multiply-linked HDI derivatives or mixtures thereof as biuret or uretdione.

When difunctional isocyanates are used, low-molecular-weight triols, for example trimethylolpropane, trimethylolethane, or even 1,2,4-butanetriol, 1,1,6-hexanetriol, or polyether, polyester, or alkanes with three or more functional OH groups can be used to improve the cross linking.

When the ferrocene derivatives according to the invention are bonded with a functional OH group, trifunctional isocyanates or difunctional isocyanates are preferably used in conjunction with a cross-linking triol. For a propellant with HTPB binder, a system composed of trimethylolpropane and IPDI is especially suited. When bonding the ferrocene derivatives according to the invention with two functional OH groups in a binder system based on hydroxy terminated prepolymers, a corresponding equivalent amount of diisocyanate is preferably used. IPDI or dimeryldiisocyanate (DDI) are recommended as curing agents for HTPB-bonded propellants. If the OH functionality of the prepolymer is two or less, cross-linking triols such as trimethylolpropane can also be used.

In a composite solid propellant with the burning rate modifier according to the invention, ammonium perchlorate (AP), ammonium nitrate (AN), potassium perchlorate, or other perchlorates as well as mixtures of these substances can be used as the oxidant. Preferably AP is added in amounts of 30 to 88 wt. % of the propellant. Other components preferably include 10 to 45 wt. % polyurethane binder, consisting of prepolymer, curing agent, and possibly further additives such as polymer-specific plasticizers, antioxidants, stabilizers, and adhesion promoters. The ferrocene derivative according to the invention is preferably contained in an amount of 0.1 to 6 wt. % in the solid propellant.

To increase the propellant energy, burning temperature, and specific momentum of the escaping gases, metallic fuels such as aluminum, magnesium, aluminum/magnesium alloys, or boron can be added to the fuel, especially in finely pulverized form, with an average grain size of 1 to 500 $\mu$m, in preferred quantities of 1 to 25 wt. % and/or energy-rich nitramines such as hexogen and/or octogen, in a preferred quantity of 1 to 40 wt. %, especially 1 to 30 wt. %. Low-energy rocket or gas generator propellants can also contain nitroguanadine.

A preferred composition of the composite solid propellant contains 40 to 88 wt. % AP, 10 to 45 wt. % polyurethane binder, 0.1 to 6.0 wt. % ferrocene derivative, and 1 to 30 wt. % metallic fuel, especially aluminum.

To produce the propellant, the liquid prepolymer is mixed with the plasticizer and the additives, the ferrocene derivative, the fuel, and the oxidizer to form a slurry and then curing agents are added with additional mixing. Preferably, production takes place in a vertical kneader whose temperature can be controlled between 30° to 60° C. and which can be evacuated, with kneading hooks or a planetary stirrer. The binder components, prepolymer, plasticizer, and additive are premixed along with the ferrocene derivative according to the invention and the triolene required for cross linking, and then the metal powder, nitramine, and finally the preheated oxidizer are added batchwise. After thorough kneading, the homogeneous pasty or flowable material is mixed with the curing agent. The resultant propellant slurry can pour and run well as a rule. For manufacturing propellant charges, it is generally poured directly into the combustion chamber or into a corresponding combustion chamber insert and allowed to cure for several hours at approximately 50° to 700° C. The propellant, when removed from the mold, exhibits good mechanical properties, is stable during storage for a long period of time, and exhibits good burning behavior.

Manufacture of 4,4'-bis( ethylferrocenyl)-1-pentanol (BEFPO)

A solution is prepared from 340.3 g methanol and 319.4 g concentrated sulfuric acid, to which 350 g of ethyl ferrocene is added. At a reaction temperature of approximately 80° C., 106.6 g of levulin acid methylester are added within 60 minutes and stirred with reflux at 80° C. for another 5 hours. Then extraction is performed, surplus sulfuric acid neutralized, and the product purified. Unreacted ethyl ferrocene and levulin acid methylester are distilled off and the remaining product is reacted with 250 ml diethylether and 50 ml tetrahydrofuran. 10 g of lithium aluminum hydride powder are added batchwise to this solution and stirred for approximately 2 hours at 35° C. with reflux. After workup and vacuum distillation, 126.1 g of the desired substance are obtained. The product is liquid at room temperature and has a comparatively low viscosity. In this form, it is processed at 60° C. to create a high-energy composite propellant with the following composition:

Manufacture and Testing of a Solid Propellant

Solid, 85 wt. % with the following composition

|  | wt. % |
|---|---|
| ammonium perchlorate 30 $\mu$m | 49 |
| ammonium perchlorate 5 $\mu$m | 21 |
| aluminum powder 5 $\mu$m | 15 |
| Binder, 15 wt. % following composition | |
| ferrocene derivative BEFPO: | 1.5 |
| hydroxy terminated polybutadiene R 45-M (Atochem): | 8.17 |
| adhesion promoter: Tepanol ® HX 878 (3M): | 0.14 |
| Curing agent: difunctional isocyanate, IPDI (Hüls): | 1.72 |

-continued

| | wt. % |
|---|---|
| Cross-linking agent: trimethylolpropane (TMP): | 0.32 |
| Antioxidant: Di-tert-butylphenol (Igranox ® 565); Ciba Geigy: | 0.15 |
| Plasticizer: diisooctyladipate (DOA): | 3.0 |

Initially the liquid ferrocene derivative (BEFPO) is premixed with binder components R45M, TMP, Tepanol®, Irganox®, and DOA and heated to 60° C. Then the preheated aluminum powder and ammonium perchlorate are added batchwise and the mass kneaded for at least 4 hours until it has become homogeneous and largely flowable. Following addition of the isocyanate curing agent IPDI and stirring for approximately 10 minutes, a propellant slurry is obtained with good pourability and good flow characteristics.

After the viscosity has been measured, the slurry is poured under vacuum into the preheated propellant mold and cured there at 60° C. for 7 to 8 days. After removal from the mold, a solid propellant is obtained with good mechanical properties. Specifically, the following properties have been found:

pouring viscosity (60° C.): 184 Pas sensitivity to friction: 36N impact sensitivity: 3 Nm Mechanical properties at 20° C. (50 mm/min)

Tensile strength: $1.34 N/mm^2$

Breaking elongation: 22%

Young's modulus: $8.62 N/mm^2$

Burning properties at 20° C.

| Burning rate r: | a) with BEFPO | b) without BEFPO |
|---|---|---|
| p = 2 MPa | 20.3 mm/s | 13.5 mm/s |
| p = 10 MPa | 36.6 mm/s | 27.3 mm/s |

Pressure exponent n: 0.34 (2–25 MPa) 0.47 (2–25 MPa)

Figure 1:
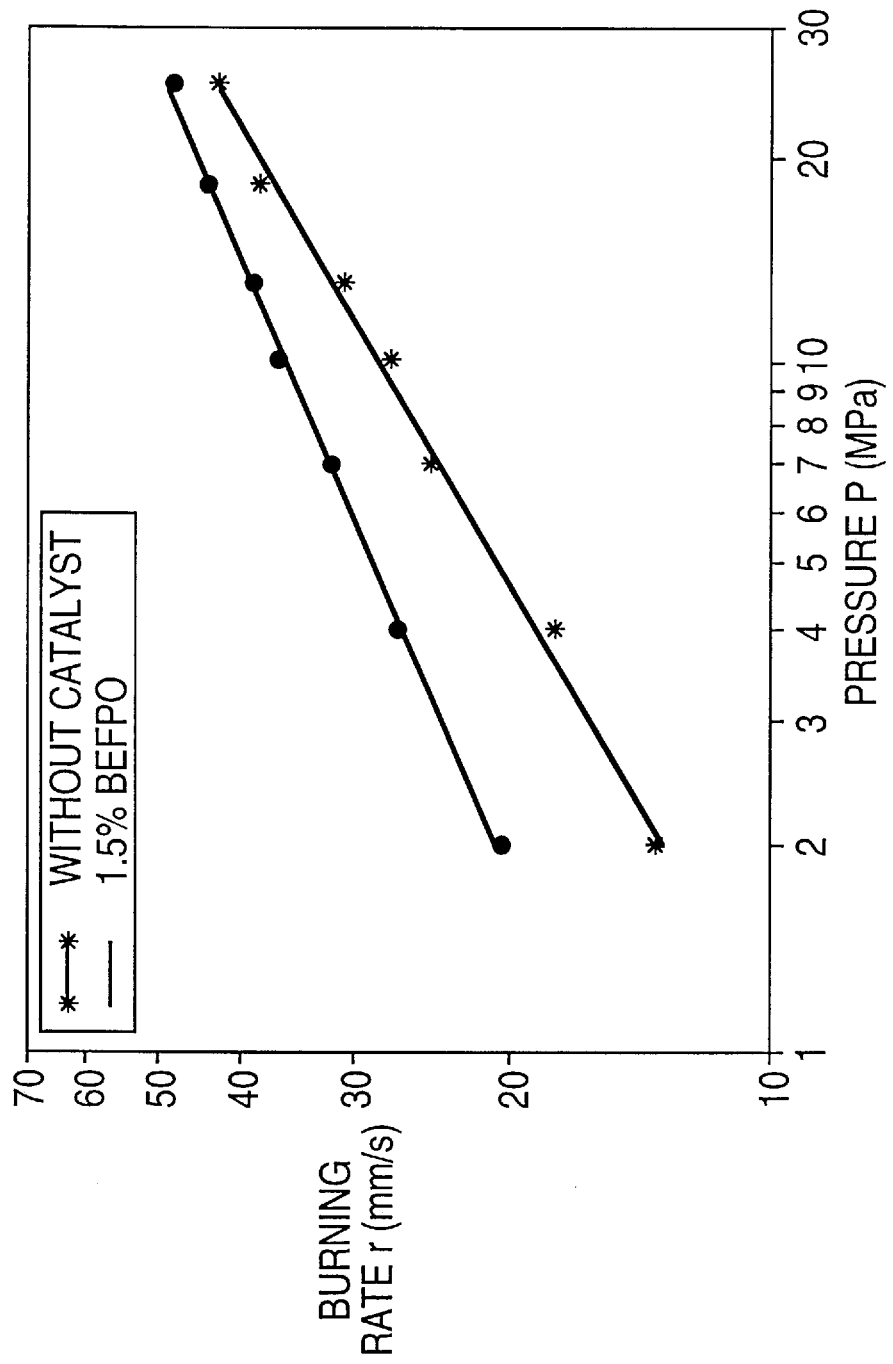
FIG. 1 also shows the burning graph log r=f (log p) of the propellant containing BEFPO in comparison to the formulation without the burning catalyst. The effect of the ferrocene derivative in accelerating burning is readily apparent.

A migration test of propellant containing BEFPO in combination with polybutadiene insulation by storage for 7 days at 80° C., after analyzing the propellant and the insulation, showed a negligibly small decrease in the iron concentration in the propellant from 0.34 to 0.33% but no perceptible increase in iron content in the insulation.

The substances according to the invention, especially BEFPO, thus meet all of the important requirements for a burning rate modifier for solid propellant, namely good workability without adversely affecting the pouring viscosity of the propellant slurry, good network formation with addition of a cross-linking triol, no adverse effect on mechanical propellant sensitivity and stability, as well as high effectiveness regarding increase in burning rate and decrease in pressure exponent.

We claim:

1. A ferrocene derivative with the general formula

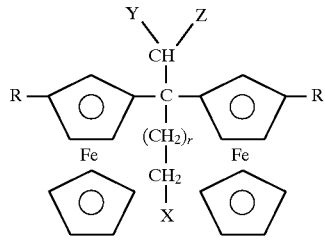

X=H or OH

Y=H or $CH_2OH$ z=$(CH2)_2$—$CH_2OH$

R=straight-chain or branched alkyl residue with 2 to 6 C atoms r=0 to 8, and s=0 to 8.

2. Composite solid propellant including the ferrocene derivative according to claim 1 as burning rate modifier.

3. Composite solid propellant according to claim 2, further including a crystalline inorganic oxidant, a polymer binder with a multiple-OH-substituted prepolymer, at least one cross-linking reagent, polymer-specific plasticizers, antioxidants, and adhesion promoters, and wherein the ferrocene derivative is coupled with the polymer binder by the at least one cross-linking reagent.

4. Composite solid propellant according to claim 3, wherein the multiple-OH-substituted prepolymer is a polyurethane prepolymer in the form of hydroxy terminated polybutadiene (HTPB), polyester polyol or polyetherpolyol.

5. Composite solid propellant according to claim 3, wherein the at least one cross-linking reagent is di- or trifunctional isocyanates.

6. Composite solid propellant according to claim 3, wherein the at least one cross-linking reagent includes difunctional isocyanates, and the propellant further includes low-molecular-weight triols, or short chain polyether, polyester, or alkanes with three or more functional OH groups each.

7. Composite solid propellant according to claim 2, wherein the solid propellant contains 10 to 45 wt. % polyurethane binder composed of prepolymer and linking reagent.

8. Composite solid propellant according to claim 3, wherein at least one of ammonium perchlorate (AP) and ammonium nitrate (AN) is used as the oxidant.

9. Composite solid propellant according to claim 3, wherein the propellant further includes a metallic fuel which is selected from the group consisting of aluminum, magnesium, an aluminum-magnesium alloy and boron.

10. Composite solid propellant according to claim 3, wherein the propellant further includes an energy-rich nitramine which is at least one of hexogen and octogen.

11. Composite solid propellant according to claim 2, wherein the ferrocene derivative is are included in the propellant in an amounts of 0.1 to 6 wt. %.

12. Composite solid propellant according to claim 3, wherein the propellant further includes at least one of a metallic and an energy-rich nitramine.

13. Composite solid propellant according to claim 6, wherein the low-molecular-weight triols are selected from the group consisting of trimethylolpropane, trimethylolethane, 1,2,4-butanetriol and 1,2,6-hexanetriol.

14. Composite solid propellant according to claim 7, wherein the propellant further includes a cross-linking reagent.

15. Composite solid propellant according to claim 8, wherein the least one of ammonium perchlorate and ammonium nitrate included in amounts of 40–88 wt. %.

16. Composite solid propellant according to claim 9, wherein the metallic fuel is included in the propellant in amounts of 1 to 30 wt. %.

17. Composite solid propellant according to claim 10, wherein the energy-rich nitramine is included in the propellant in amounts 1 to 30 wt. %.

18. Composite solid propellant according to claim 5, wherein the di- or trifunctional isocyanate are selected from the group consisting of isophorondiisocyanate (IPDI), dimeryldiisocyanate (DDI), hexamethylenediisocyanate (HDI), toluene diisocyanate (TDI), and multiply-linked HDI derivatives or mixtures thereof as biuret or uretdione.

19. The ferrocene derivative according to claim 1, wherein r is 0 to 2.

20. The ferrocene derivative according to claim 1, wherein s is 1 or 2.

21. The ferrocene derivative according to claim 1, wherein s is 1 or 2.

22. Composite solid propellant according to claim 2, further including a polymer binder with a multiple-OH-substituted prepolymer, wherein the multiple-OH-substituted prepolymer is a polyurethane prepolymer in the form of hydroxy terminated polybutadiene (HTPB), polyester polyol or polyether polyol.

23. Composite solid propellant according to claim 22, wherein said prepolymer has an OH functionality of 2 to 3.

24. Composite solid propellant according to claim 2, comprising 0.1 to 6.0 wt. % of said ferrocene derivative, 40 to 88 wt. % ammonium perchlorate, 10 to 45 wt. % polyurethane binder and to 30 wt. % metallic fuel.

25. Composite solid propellant according to claim 24, wherein said metallic fuel is aluminum.

* * * * *